(12) United States Patent
Chung et al.

(10) Patent No.: US 10,870,831 B2
(45) Date of Patent: Dec. 22, 2020

(54) METHOD FOR INDUCING DIFFERENTIATION OF NEURAL STEM CELLS USING PATTERNED HYDROGEL

(71) Applicant: SOGANG UNIVERSITY RESEARCH FOUNDATION, Seoul (KR)

(72) Inventors: Bong Geun Chung, Gyeonggi-do (KR); Jong Min Lee, Seoul (KR); Joo Yoon Moon, Gyeonggi-do (KR); Tae Hyeon Kim, Seoul (KR); Daniel Christian Ahrberg, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 224 days.

(21) Appl. No.: 15/736,418

(22) PCT Filed: Mar. 10, 2017

(86) PCT No.: PCT/KR2017/002645
§ 371 (c)(1),
(2) Date: Dec. 14, 2017

(87) PCT Pub. No.: WO2018/088639
PCT Pub. Date: May 17, 2018

(65) Prior Publication Data
US 2019/0062701 A1    Feb. 28, 2019

(30) Foreign Application Priority Data

Nov. 11, 2016  (KR) .................. 10-2016-0150508

(51) Int. Cl.
*C12N 5/0793* (2010.01)
*C12N 13/00* (2006.01)
*C12N 5/00* (2006.01)
*C12N 5/0797* (2010.01)

(52) U.S. Cl.
CPC ......... *C12N 5/0619* (2013.01); *C12N 5/0068* (2013.01); *C12N 5/0623* (2013.01); *C12N 13/00* (2013.01); *C12N 2500/10* (2013.01); *C12N 2500/50* (2013.01); *C12N 2529/00* (2013.01); *C12N 2533/30* (2013.01); *C12N 2535/00* (2013.01)

(58) Field of Classification Search
CPC ...... A61L 27/54; A61L 27/52; A61L 2300/64; A61L 2300/62; A61L 2400/12; A61L 2420/08; A61L 27/04; A61L 27/24; C12N 5/0619; C12N 5/0068; C12N 5/0623; C12N 13/00; C12N 2529/00; C12N 2500/10; C12N 2500/50; C12N 2535/00; C12N 2533/30; C12N 2533/00; C12N 2506/08

See application file for complete search history.

(56) References Cited

FOREIGN PATENT DOCUMENTS

CA       2408172       * 11/2001

OTHER PUBLICATIONS

Tandon et al., 35th Annual International Conference of the IEEE EMBS, Osaka, Japan, Jul. 3-7, 2013 (Year: 2013).*
Cordey et al. Stem Cells 26:2586-2594, 2008 (Year: 2008).*
Fattahi et al., Adv Mater, 26(12):1846-1885, Mar. 2014 (Year: 2014).*
Serena, E., et al. "Electrical stimulation of human embryonic stem cells: Cardiac differentiation and the generation of reactive oxygen species", Experimental Cell Research, Author Manuscript, 2009, 315(20), pp. 3611-3619.
Woo, D.G., et al. "The effect of electrical stimulation on the differentiation of hESCs adhered onto fibronectin-coated gold nanoparticles". Biomaterials 2009, 30(29): pp. 5631-5638.
Pires, F., et al. "Neural stem cell differentiation by electrical stimulation using a cross-linked PEDOT substrate: Expanding the use of biocompatible conjugated conductive polymers for neural tissue engineering". Biochimica et Biophysica Acta 2015, 1850(6): pp. 1158-1168.
Prabhakaran, M. P., et al. "Electrospun conducting polymer nanofibers and electrical stimulation of nerve stem cells". Journal of bioscience and bioengineering 2011, 112(5): pp. 501-507.
Huang, Y. J., et al. "Carbon nanotube rope with electrical stimulation promotes the differentiation and maturity of neural stem cells". Small 2012, 8(18): pp. 2869-2877.
Liu, X., et al. "Electrical stimulation promotes nerve cell differentiation on polypyrrole/poly (2-methoxy-5 aniline sulfonic acid) composites". Journal of Neural Engineering, 2009, 6(6): pp. 1-10.
Yamada, M., et al. "Electrical stimulation modulates fate determination of differentiating embryonic stem cells". Stem Cells 2007, 25(3): pp. 562-570.
Choi, Y. Y., et al. "Controlled-size embryoid body formation in concave microwell arrays". Biomaterials 2010, 31(15): pp. 4296-4303.
2016 Annual Fall Meeting of the Korean BioChip Society Program, "Future Biochips @ Industry", Oct. 26, 2016.

* cited by examiner

*Primary Examiner* — Kimberly Ballard
*Assistant Examiner* — Stacey N MacFarlane
(74) *Attorney, Agent, or Firm* — Harness, Dickey & Pierce, P.L.C.

(57) ABSTRACT

The present invention provides a method for inducing differentiation of neural stem cells. The present invention provides optimized differentiation conditions of neural stem cells into neurons using a patterned hydrogel.

7 Claims, 6 Drawing Sheets
(4 of 6 Drawing Sheet(s) Filed in Color)

METHOD FOR INDUCING DIFFERENTIATION OF NEURAL STEM CELLS USING PATTERNED HYDROGEL

CROSS-REFERENCE TO RELATED APPLICATIONS

This application is a national phase application of PCT Application No. PCT/KR2017/002645 filed on Mar. 10, 2017, which claims the benefit and priority of Korean Application No. 10-2016-0150508 filed on Nov. 11, 2016. The entire disclosures of the applications identified in this paragraph are incorporated herein by reference.

FIELD

The present invention was made with the support of the Ministry of Science, ICT, and Future Planning of the Republic of Korea, under Project No. 2016M3A7B4910652, which was conducted under the research project entitled "Development of Microfluidic Chip for Mold Detection" within the project named "Nano-material Source Technology Development Project" by Sogang University under the management of the National Research Foundation of Korea, from 1 Aug. 2016 to 28 Feb. 2017.

The present invention was made with the support of the Ministry of Education of the Republic of Korea, under Project No. 2016R1A6A1A03012845, which was conducted under the research project entitled "Development of Nano-biochip Having Function of Evaluating Brain Disease Drug" within the project named "Basic Research Project (Focused Business of Research)" by Sogang University under the management of the National Research Foundation of Korea, from 1 May 2016 to 31 Dec. 2016.

The present invention was made with the support of the Ministry of Education of the Republic of Korea, under Project No. 2016R1A6A3A11931838, which was conducted under the research project entitled "Development of Wearable Device technology for Nerve Regeneration Research" within the project named "Research Fellow" by Sogang University under the management of the National Research Foundation of Korea, from 1 Nov. 2016 to 31 Oct. 2017.

The present invention relates to a method for inducing differentiation of neural stem cells using patterned hydrogel.

BACKGROUND

Neural stem cells are derived from the central nervous system, have self-renewal ability, have no characteristics of differentiated cells, and have potency to differentiate into various cells of the nervous system. When nervous tissues are damaged, neural stem cells have the flexibility to differentiate into damaged nervous tissues, are self-reproducing and immunologically safe in the implanted body. The death of neurons is a hallmark of neurodegenerative diseases and severe central nervous system diseases. In addition, the decrease of cells is caused by the absence of regenerative capacity for the replacement or therapy of damaged cells in the central nervous system. One way to overcome such problems is cell replacement therapy using reproducible neural stem cells.

To optimize these cell therapy conditions, cell and tissue culture studies can be carried out using micro-processing technology as a semiconductor manufacturing process. Micro-processing technology is actively being studied in various fields. Micro-processing technology has excellent efficiency and productivity, and can be implemented at low cost. In addition, the microenvironment around neurons can be precisely controlled since microstructures suitable for cell or tissue studies can be fabricated. The proliferation and differentiation of neural stem cells are highly affected by the microenvironment, such as growth factors and signal substances, and therefore, it is important to control the microenvironments.

An existing method for stem cell research in a three-dimensional organization is limited because the method has difficulty in making a complicated environment with accuracy and reproducibility. Therefore, there is a need of technology capable of optimizing various conditions compared with existing patterning-related technology.

Throughout the entire specification, many papers and patent documents are referenced and their citations are represented. The disclosure of cited papers and patent documents is entirely incorporated by reference into the present specification, and the level of the technical field within which the present invention falls and details of the present invention are explained more clearly.

DETAILED DESCRIPTION

Technical Problem

The present inventors endeavored to optimize the conditions of differentiation of neural stem cells into neurons using a patterned hydrogel. As a result, the present inventors confirmed that the use of a hydrogel, which was patterned to have a predetermined interval, resulted in excellent differentiation of neural stem cells into neurons, and optimized the conditions of spatial and electric stimulations to neural stem cells, and therefore completed the present invention.

Accordingly, an aspect of the present invention is to provide a method for inducing differentiation of neural stem cells.

Other purposes and advantages of the present disclosure will become more obvious with the following detailed description of the invention, claims, and drawings.

Technical Solution

In accordance with an aspect of the present invention, there is provided a method for inducing differentiation of neural stem cells, the method including:

(a) culturing neural stem cells to induce neurospheres;

(b) seeding the neurospheres on a cell culture substrate on which a hydrogel comprising a biocompatible polymer and a conductive nanowire is patterned to have intervals of 150-250 μm; and (c) applying voltage to the cell culture substrate to induce the differentiation into neurons.

(d) obtaining the neurons.

The present inventors endeavored to optimize the conditions of differentiation of neural stem cells into neurons using patterned hydrogel. As a result, the present inventors confirmed that the use of a hydrogel, which was patterned to have a predetermined interval, resulted in excellent differentiation of neural stem cells into neurons, and optimized the conditions of spatial and electric stimulations to neural stem cells.

The method for inducing differentiation of neural stem cells of the present invention will be described by steps.

Step (a): Inducing Neurospheres

First, neural stem cells are cultured to induce neurospheres.

As used herein, the term "neural stem cells" refers to undifferentiated cells having potency to differentiate into any cells constituting the central nervous system, such as neurons, astrocytes, or oligodendrocytes.

The specific separation of the neural stem cells is disclosed in U.S. Pat. No. 5,654,183, which is incorporated herein by reference. Neural stem cells may be cultured by adding, to a medium, a growth factor, such as a basic fibroblast growth factor (bFGF), an epidermal growth factor (EGF), or a fibroblast growth factor (FGF), at an appropriate concentration range, for example, 5-100 ng/ml.

The neural stem cells of the present invention may preferably be primary cultured neural stem cells which are isolated and cultured from human tissues, or an immortalized stem cell line established by introducing, into the primary cultured neural stem cells, a vector including a tumor gene (e.g., v-myc gene) in a form capable of being expressed.

The neural stem cells may be cultured in a floating state in a culture medium lacking cell-adherent substrates, thereby obtaining neurospheres. The neurospheres have an aggregation form of neural stem cells.

According to an embodiment of the present invention, the neurospheres have a size of 100-150 µm. Such a size is suitable for culture in a patterned hydrogel.

The present invention further includes a step of coating an extracellular matrix (e.g., laminin and poly-L-ornithine) on a cell culture substrate on which the hydrogel is patterned, so that cells adhere to the cell culture substrate.

Step (b): Seeding Neurospheres

Then, the neurospheres are seeded on a cell culture substrate on which a hydrogel comprising a biocompatible polymer and a conductive nanowire is patterned to have intervals of 150-250 µm.

The major characteristic of the present invention is that neural stem cells are differentiated using a cell culture substrate on which a hydrogel is patterned to have intervals of 150-250 µm.

According to an embodiment of the present invention, the patterned hydrogel have intervals of 160-240 µm, 170-230 µm, 180-220 µm, or 190-210 µm.

The substrate is a film, glass, plastic, or silicone.

As verified in the following examples, the substrate is a film. In order to facilitate the utilization of neurons prepared by the present invention, the present inventors differentiated neurospheres by patterning a hydrogel on a flexible substrate.

The intervals of the patterned hydrogel influence the differentiation efficiency of neurospheres. The more suitable the pattern is for the size of the neurospheres, the better the differentiation into neurons is.

The hydrogel comprises a biocompatible polymer and a conductive nanowire.

Any biocompatible polymer that is known in the art may be used as the biocompatible polymer of the present invention, but according to an embodiment of the present invention, the biocompatible polymer is selected from the group consisting of polyethylene glycol (PEG), dextran, albumin, polyvinyl alcohol, polyethyleneimine, polylactic-glycolic acid (PLGA), polylactic acid, polylactides, polyglycolic acid, polyamino acids, polyacetals, polyorthocarbonates, polycarbonates, polycarbolactone polyacrylic acid, polymethacrylic acid, polysaccharides, polyketals, polyethers, polyamides, polymaleic anhydrides, poly methyl vinyl ethers, and copolymers of the polymers.

As verified in the following examples, the biocompatible polymer constituting the hydrogel is polyethylene glycol.

According to an embodiment of the present invention, the conductive nanowire is a metal nanowire. According to another embodiment of the present invention, the metal nanowire is a silver nanowire, a copper nanowire, a gold nanowire, or an aluminum nanowire.

For example, in cases where PEG is mixed with a different material and then photo-crosslinking is conducted by UV irradiation, the volume increase of the different material interferes with photo-crosslinking. Here, the nanowire has a large surface area compared with the volume thereof, and thus does not interfere with photo-crosslinking and has high conductivity, and therefore, the nanowire is suitable for the preparation of the patterned hydrogel of the present invention.

The hydrogel in step (b) comprises a biocompatible polymer and a conductive nanowire at a mixing ratio of 8-12:1.

According to examples, the mixture liquid of PEG and a silver nanowire forms photo-crosslinkage from a ratio of 10:1, and if the ratio exceeds 10:1, for example, the ratio is 5:1, PEG is not gelated.

According to an embodiment of the present invention, the hydrogel comprises a biocompatible polymer and a conductive nanowire at a ratio of 9-12:1, 10-12:1, 9-11:1, or 10:1.

Step (c): Inducing Differentiation into Neurons

Then, a voltage is applied to the cell culture substrate to induce the differentiation into neurons.

The present inventors tried to find out a voltage condition suitable for the differentiation of neural stem cells.

According to an embodiment of the present invention, the voltage is 8-12 V.

According to another embodiment of the present invention, the voltage is 9-12 V, 9-11 V, or 10 V.

As verified in the following examples, it was confirmed that the differentiation of neural stem cells was better attained in a voltage condition of 10 V compared with a voltage condition of 5 V and 20 V.

It was confirmed through simulation that a current flowed through micropatterns when a voltage was applied to both ends of a culture medium containing the cell culture substrate therein. When a voltage of 10 V was applied, the average value of the current flowing through pattern walls was calculated according to each material of the micropatterns. As a result, it was confirmed that the largest current flowed through micropatterns formed of 10% PEG containing AgNW. The average value of the current flowing through pattern walls was calculated according to each applied voltage.

According to an embodiment of the present invention, the cell culture substrate in step (c) has an average current value of 10-20 nA. According to another embodiment of the present invention, the average current value is 12-20, 14-20, 12-18, 12-17, or 14-17 nA.

Step (d): Obtaining Neurons

Last, the neurons are obtained.

SUMMARY

The features and advantages of the present invention are summarized as follows:

(a) The present invention provides a method for inducing differentiation of neural stem cells.

(b) The present invention provides optimized conditions of differentiation of neural stem cells into neurons using the patterned hydrogel.

BRIEF DESCRIPTION OF THE DRAWINGS

The patent of application file contains at least one drawing executed in color. Copies of this patent or patent application publication with color drawings(s) will be provided by the office upon request and payment of the necessary fee.

FIG. 1A is a schematic diagram of a conductive hydrogel patterning method and electric stimulation. FIG. 1B is an image of a PET film with a patterned conductive hydrogel. FIG. 1C shows Fluorescent microscopy image of AgNW/hydrogel after removal of the PDMS mold, for visualization the hydrogel has stained with fluorescein; scale bar is 100 μm.

FIGS. 2A, 2B and 2C are SEM images of 10% PEG, AgNW, and a mixture of 10% PEG and AgNW, respectively; and FIG. 2D illustrates the results of ingredient analysis of the mixture containing AgNW.

FIG. 3A shows a two-hour-interval electric stimulation function using a function generator; and FIG. 3B shows simulation of formation of average current density in a 6-well plate FIG. 3C shows the measurement results of the amount of current flowing through patterns according to each material. FIG. 3D shows the measurement results of current density in PEG/AgNW patterns according to each voltage.

FIG. 6A is an analysis graph of the direction and growth of neurites in the pattern-less control and on the patterns at the application of a voltage of 0, 5, 10, and 20 V. FIG. 6B is an analysis graph of the direction and growth of neurites in PEG/AgNW patterns at the application of each voltage. FIG. 6C is a comparative analysis graph of the direction and growth of neurites in neurons at the application of 10 V in the control and on the patterns.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Materials and Methods
Fabrication of Patterned Hydrogel

The present inventors developed a technique to induce the differentiation of stem cells using hydrogel patterning technology. The application of electric stimulation to stem cells can induce the differentiation into neurons, and thus, the present inventors employed photolithography technology, which corresponds to a semiconductor manufacturing process, in order to manufacture a device for providing electric stimulation. A micro-mold was fabricated of poly(dimethylsiloxane) (PDMS) using a photoresist-patterned silicon wafer, and poly(ethylene glycol) (PEG) (1000 Da, Sigma-Aldrich) and a conductive silver nanowire (AgNW, Nanopyxis CO., Ltd., composed of 0.5-2.0% of silver, 2.5-10% of acetone, 87.85-96.85% of isopropyl alcohol, and 0.15% of polyvinyl pyrrolidone) were used. A mixture was prepared by mixing the PEG and silver nanowire at a ratio of 10:1.

Figure 1:
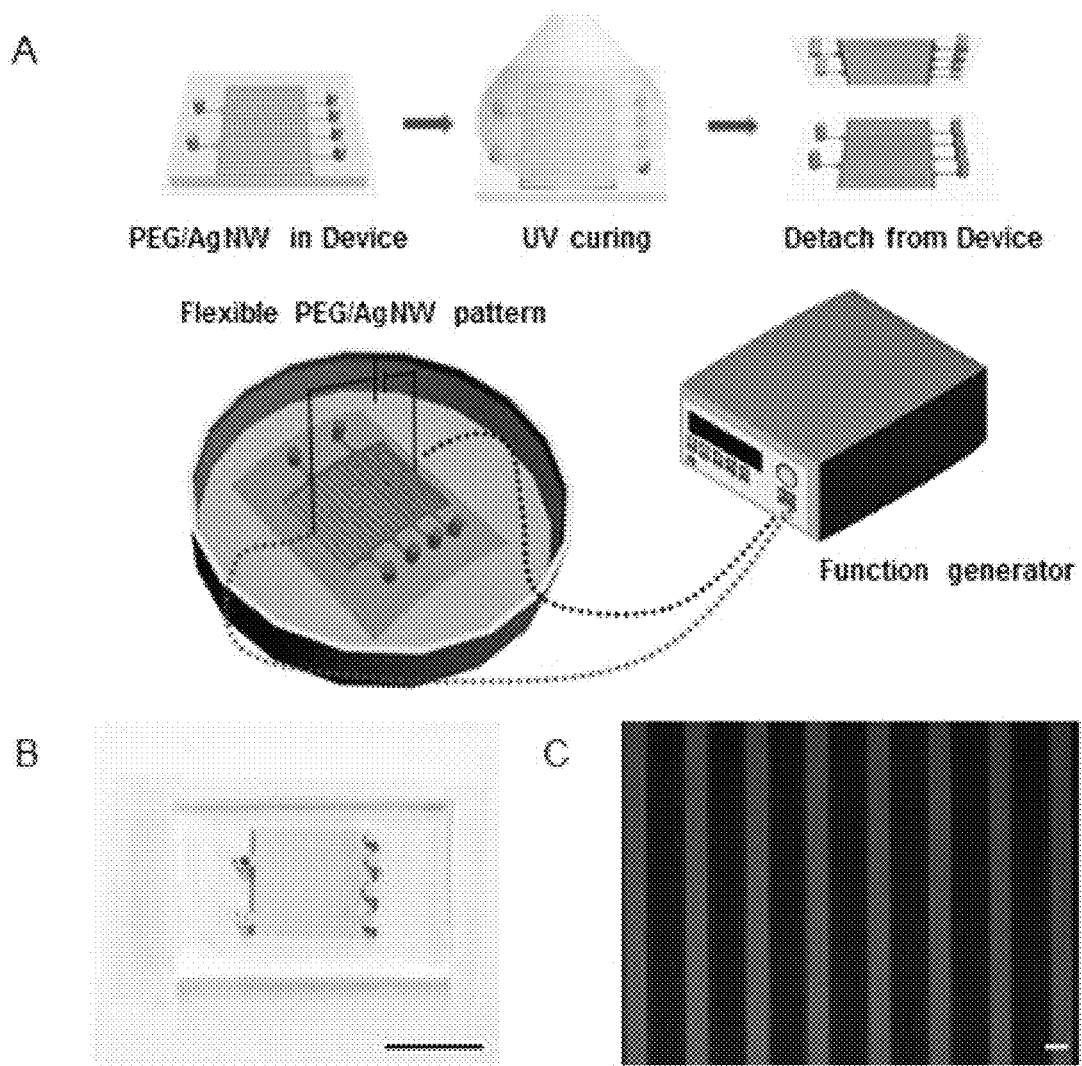
FIG. 1 shows a schematic diagram of a conductive hydrogel patterning method and electric stimulation and an image of a PET film with a patterned conductive hydrogel.
Figure 2:
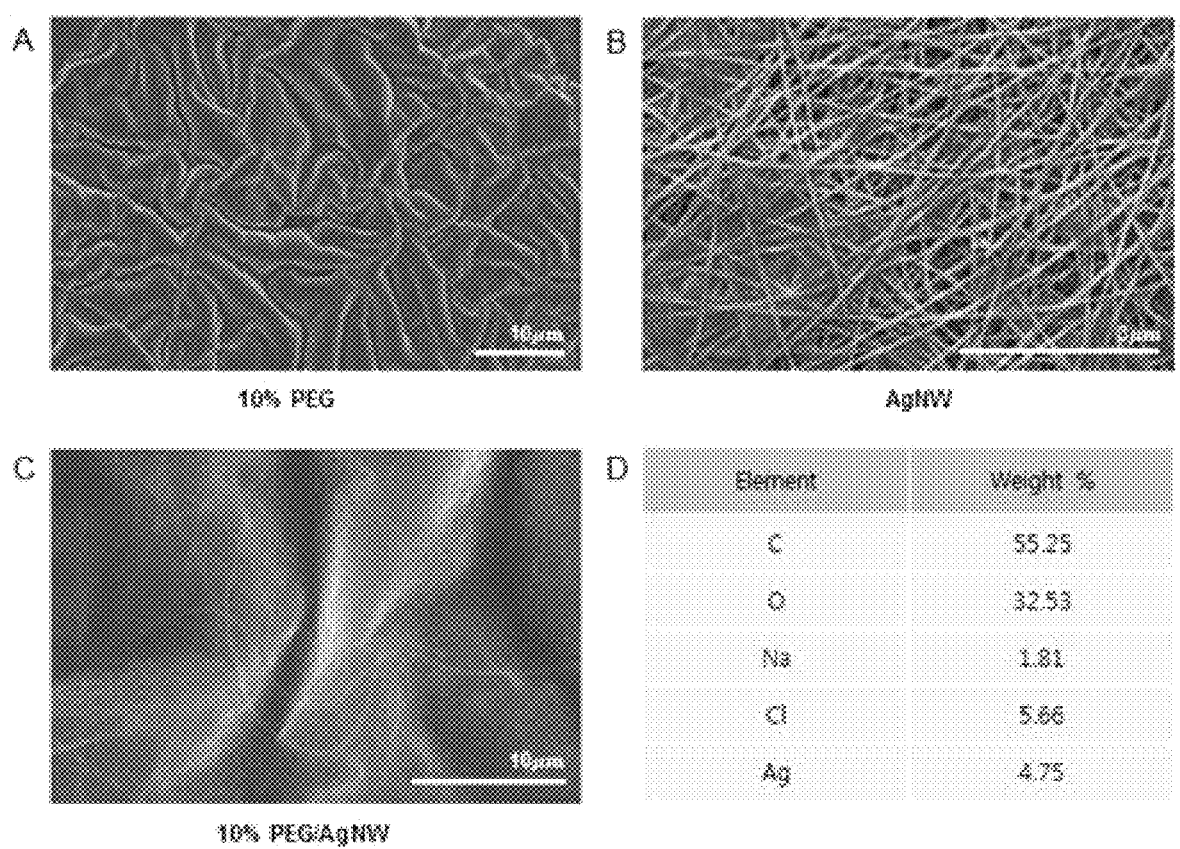
FIG. 2 shows images of PEG and AgNW (silver nanowire) constituting a conductive hydrogel.

In addition, 1 w/v % of 2-hydroxy-2-methyl propiophenone (Sigma-Aldrich Co., MO, USA) as a photoinitiator was mixed with 10 w/v % of PEG-diacrylate (1000 Da), and then mixed with a silver nanowire aqueous solution at a ratio of 10:1, thereby fabricating a PDMS micro-mold. Patterns were formed at intervals of 150, 200, and 300 μm on flexible PET film (100 microns, Filmbank) using the fabricated PDMS micro-mold, thereby manufacturing a device. For a manufacturing method, the patterning was conducted by punching the PDMS micro-mold using a punch to form inlet and outlet holes, allowing PDMS and PET film to adhere to each other, injecting a PEG/AgNW mixed material into the inlet holes using a pipette, and then performing photo-crosslinking through UV irradiation (FIG. 1). In the patterned hydrogel, a bottom surface was made of a PET film, and wall surfaces were made of a hydrogel containing a silver nanowire as a conductive material. Thereafter, a surface of the patterned device was coated with laminin and poly-L-ornithine (PLO), which are extracellular matrixes, to induce the differentiation of stem cells. Specifically, 200 ml of 0.1 mg/ml PLO was treated on the patterns using a micropipette, followed by incubation in a 37° C. incubator for 6 hours. For induction of cell differentiation, 200 ml of 0.02 mg/ml laminin was treated on the PLO-treated patterns, followed by incubation in a 37° C. incubator for 2 hours.

Culture of Neural Stem Cells

Neural stem cells (pregnant female C57BL/6 mice cerebral cortex from brain at E12 were purchased from DAEHAN BIOLINK) were cultured in N2 medium (1% serum-free N2, 2% B27 supplement, and 1% penicillin-streptomycin in DMEM/F12) containing bFGF and EGF for 3 days to allow cells to form neurospheres. When cultured in a cell culture dish for 3 days, the neural stem cells naturally agglomerated to form a neurosphere form. When cultured for 3 days, the size of neurospheres was about 100-150 micrometers.

The neurospheres were seeded on the patterned hydrogel. After the neurospheres cultured in a 6-well plate for 3 days were seeded on the patterned hydrogel using a pipette, the plate was gently shaken to allow the neurospheres to adhere between patterns. For a control, the neurospheres were seeded on the unpatterned PET film.

Induction of Differentiation of Neural Stem Cells

In the culture containing neurospheres seeded on the patterned hydrogel, the neural stem cells were subjected to electric stimulation of 5, 10, or and 20 V at intervals of 2 hours for 7 days using an AC power supply and function generator, and thereby, a test was conducted to investigate at which voltage the neural stem cells were well differentiated into neurons.

Immunostaining

The neurospheres differentiated on the patterned hydrogel were immunostained with a neural marker. The neurospheres were fixed by treatment with 4% paraformaldehyde at room temperature for 30 minutes. Then, the neurospheres were permeabilized with 1% Tripton X-100 (in PBS) at room temperature for 20 minutes. For reduction of non-specific protein binding, the neurospheres were blocked with bovine serum albumin (BSA, Sigma-Aldrich, Mo., USA) at room temperature for 4 hours. The blocked neurospheres were incubated with anti-neuronal class III β-tubulin (Tuj1, Stem cell technology, Canada) at 4° C. overnight. The neurospheres were washed three times with PBS, and incubated with Alexa Flour 488 secondary antibody at 4° C. for 4 hours. Then, cell nuclei were contrast-stained with 4',6-diamidino-2-phenylindole dihydrochloride (DAPI, Invitrogen, CA, USA). Fluorescence was observed using a confocal laser microscope (LSM 710, Carl Zeiss, Germany).

Finite Element Analysis

Figure 3:
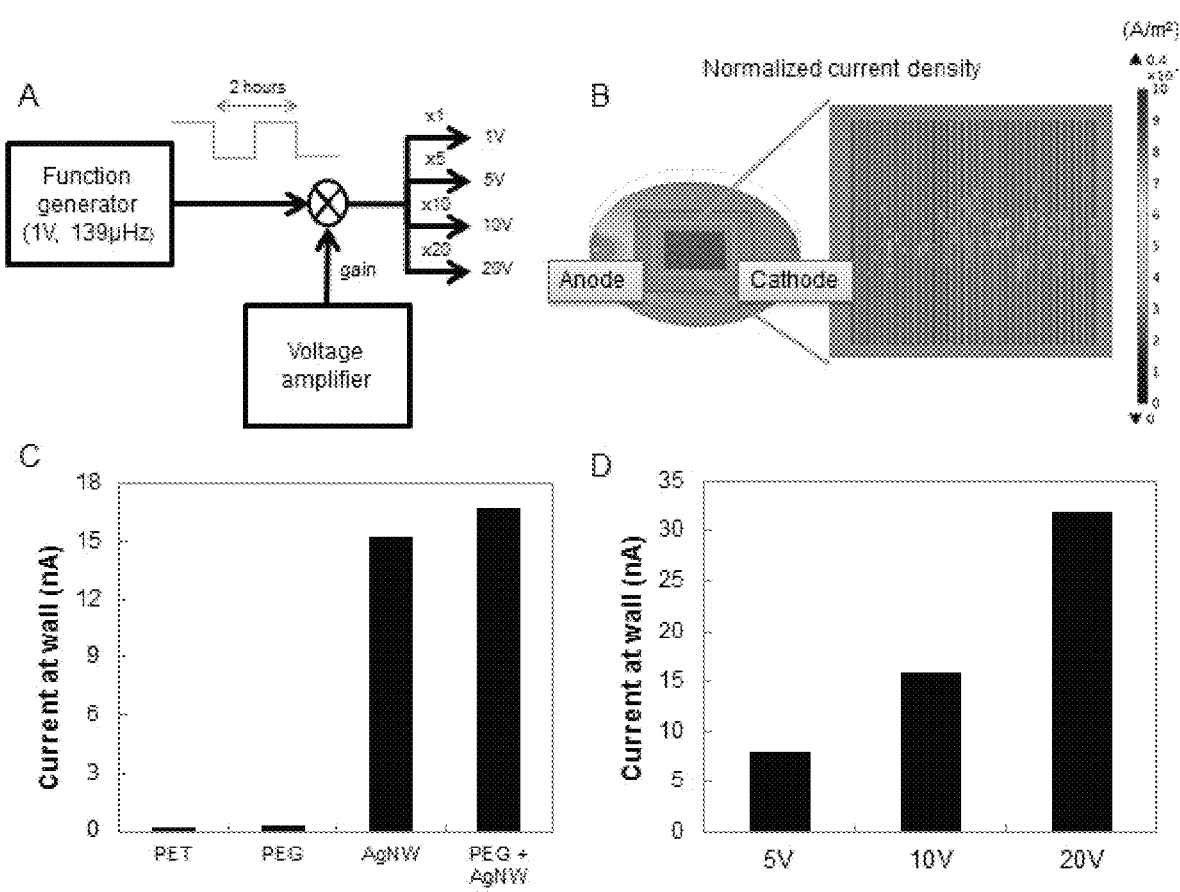
FIG. 3 shows the results of electric field measurement using simulation for electric stimulation to neural stem cells.

For application of 5, 10, or 20 V at intervals of 2 hours, an electric waveform with a frequency of 139 µHz and a voltage of 1 V was output using a function generator, and amplified 5, 10, and 20 times through a voltage amplifier (FIG. 3A). The current density flowing through 10% PEG micro-patterns containing AgNW was calculated through simulation (FIG. 3B). As a result, it was confirmed that current flowed through only the micro-patterns. In addition, when a voltage of 10 V was applied, the average current flowing through the walls was calculated according to the type of micro-pattern (FIG. 3C). The electrical conductivity was 8.6 E-17 S/cm and average current was 0.242 nA for PET; the electrical conductivity was 1.87 E-9 S/cm and average current was 0.267 nA for PEG; the electrical conductivity was 8,000 S/cm and average current was 15.2 nA for AgNW; and the electrical conductivity was 8,130 S/cm and average current was 16.7 nA for a hydrogel containing AgNW. Therefore, the higher the electrical conductivity, the higher the current value flowing through patterns. Here, the average current value is expressed by a product of the current density and the wall width, and the wall width of the micro-pattern was 0.92 mm$^2$. In addition, the average current was calculated according to each of the applied voltage (FIG. 3D). Here, the average current was 7.97 nA when 5 V was applied, the average current was 15.9 nA when 10 V was applied, and the average current was 31.9 nA when 20 V was applied. The resistance value by Ohm's law was calculated by dividing the voltage value by the current value. As a result, the resistance value was 0.627Ω.

Results

Figure 4:
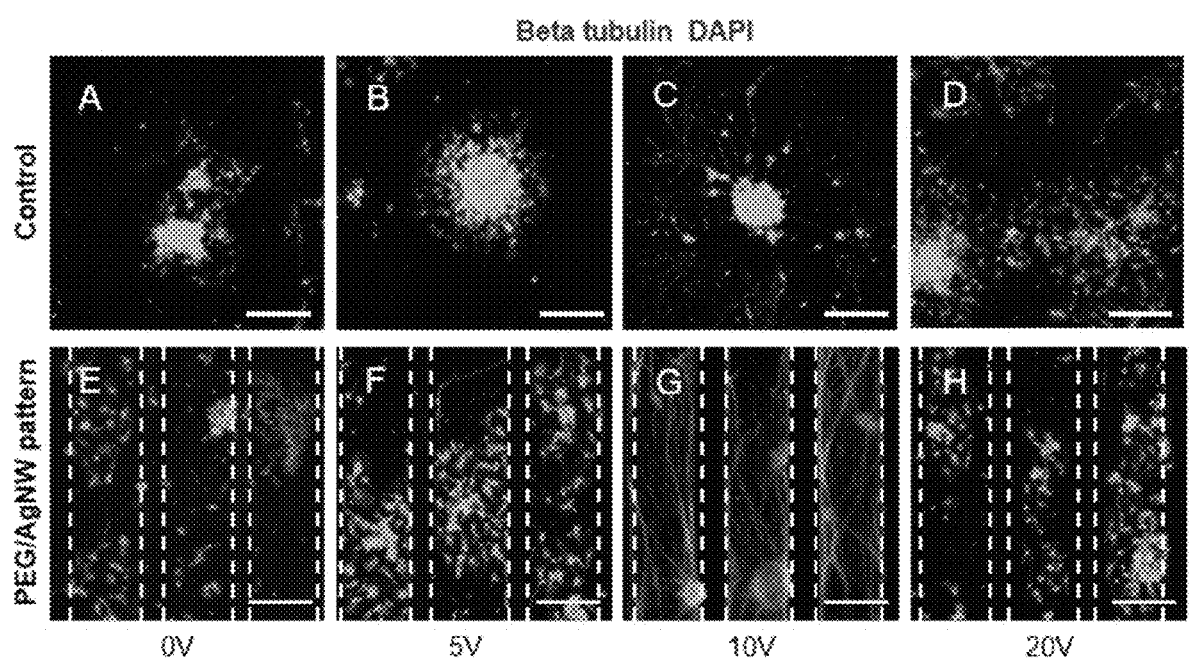
FIG. 4 shows the immunostaining results for confirming the differentiation of neurospheres into neurons by electric stimulation. The images show the differentiation into neurons according to the application of 0, 5, 10, or 20 V in a pattern-less control and the differentiation into neurons according to the application of 0, 5, 10, or 20 V in PEG/AgNW patterns.
Figure 5:
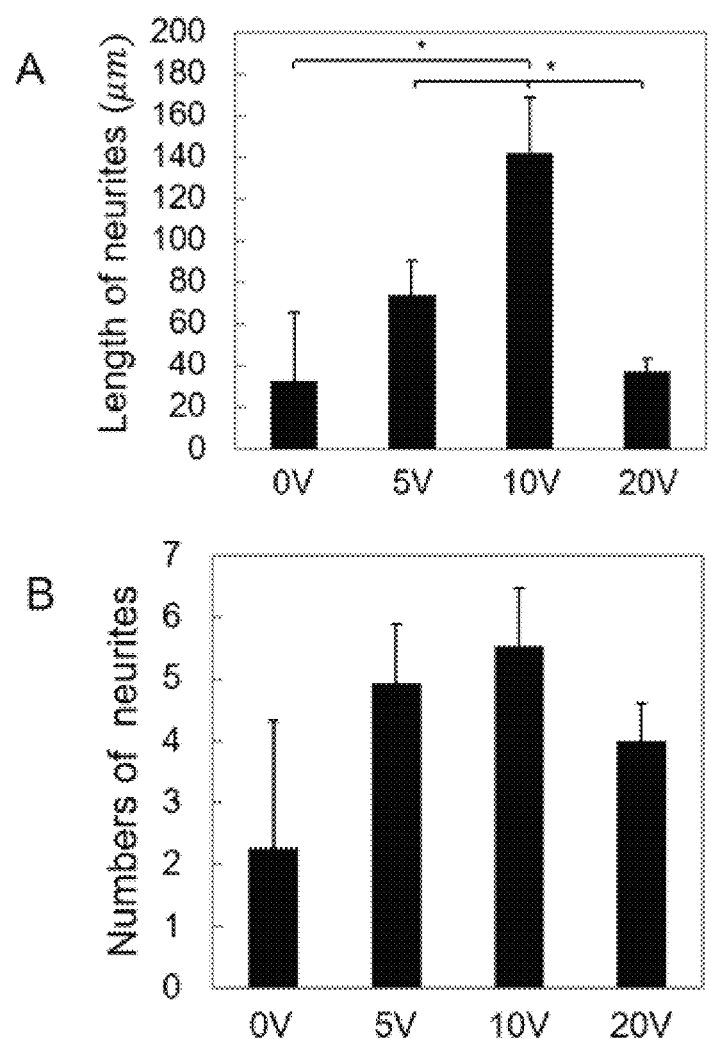
FIG. 5 shows the analysis results of the length and number of neurites in neurons by electric stimulation.
Figure 6:
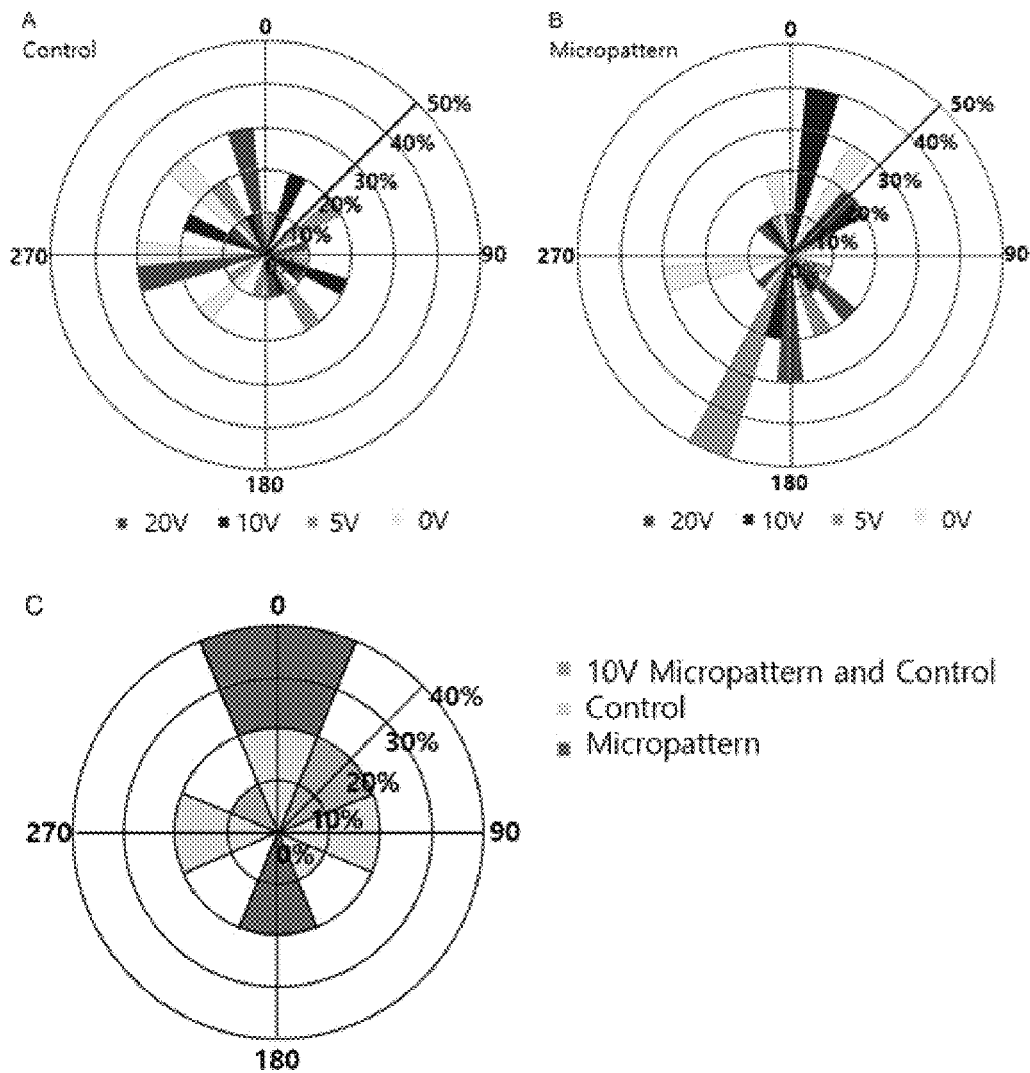
FIG. 6 shows analysis graphs of the length, number, and direction of neurites on the basis of the results of FIG. 5.

FIG. 4 shows the results of differentiation of neural stem cells into neurons when 5, 10, or 20 V was applied. Test was conducted in two conditions of a pattern-less control and AgNW patterns. The neurospheres were better differentiated into neurons on the PEG/AgNW patterns when compared with the pattern-less control, and many of long neurites were observed on the PEG/AgNW patterns especially when 10 V was applied. FIG. 5A shows the comparative analysis results of the length of neurites according to each voltage on the AgNW patterns. The analysis results confirmed that the length of the neurites increased as the voltage increased to 10 V, and again decreased at 20 V. FIG. 5B shows the analysis results of the number of neurites according to each voltage. The number of neurites increased at 5, 10, and 20 V rather than 0 V, and the number of neurites was greatest when 10 V was applied. FIGS. 6A to 6C show that the growth direction of neurites was analyzed on the control and the AgNW patterns using the Rose diagram. The neurites in the control (FIG. 6A) were grown in unspecified directions, but the neural stem cells (FIG. 6B) on the AgNW patterns at 5 V and 10 V were grown in pattern directions. In FIG. 5C, as a result of analysis of the directivity and length of neurites at 10 V, it was confirmed that the length of neurites definitely increased compared with the control and 60% of neurites grew toward the patterns when electric stimulation of 10 V was applied to stem cells.

As a test result, it was confirmed that the differentiation into neurons was well attained when electric stimulation was applied at 10 V rather than 5 V and 20 V. This fact verified that the role of spatial and electrical stimulation is important in cell differentiation.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for inducing differentiation of neural stem cells, the method comprising:
    (a) culturing neural stem cells to induce neurospheres;
    (b) seeding the neurospheres on a cell culture substrate on which a hydrogel comprising a biocompatible polymer and a conductive nanowire is patterned to have intervals of 150-250 µm; and
    (c) applying voltage to the cell culture substrate to induce the differentiation into neurons,
    wherein the conductive nanowires are patterned by mixing with the biocompatible polymer, and fixed by photocrosslinking of the biocompatible polymer, and
    wherein the hydrogel in step (b) comprises a biocompatible polymer and a conductive nanowire at a mixing ratio of 8-12:1.

2. The method of claim 1, wherein the neurospheres in step (a) have a size of 100-150 µm.

3. The method of claim 1, wherein the biocompatible polymer in step (b) is polyethylene glycol (PEG).

4. The method of claim 1, wherein the conductive nanowire in step (b) is a metal nanowire.

5. The method of claim 4, wherein the metal nanowire is a silver nanowire, a copper nanowire, a gold nanowire, or an aluminum nanowire.

6. The method of claim 1, wherein the voltage in step (c) is 8-12 V.

7. The method of claim 1, wherein the cell culture substrate in step (c) has an average current value of 10-20 nA.

* * * * *